United States Patent [19]

Csillik et al.

[11] Patent Number: 4,602,909
[45] Date of Patent: Jul. 29, 1986

[54] IONTOPHORESIS INTERMEDIARY MATERIAL AND CONTACT SOLUTION FOR THE TREATMENT OF CHRONIC PAIN SYNDROMES

[75] Inventors: Bertalan Csillik; Erzsébet Knyihár; Attila Szücs, all of Szeged

[73] Assignee: Richter Gedeon Vegyeszeti Gyar RT, Budapest, Hungary

[21] Appl. No.: 464,573

[22] Filed: Feb. 7, 1983

[30] Foreign Application Priority Data

Feb. 9, 1982 [HU] Hungary .................... 384/82

[51] Int. Cl.$^4$ ............................................ A61K 31/40
[52] U.S. Cl. ........................................ 604/20; 514/283; 514/863
[58] Field of Search .................... 514/283, 863; 604/20

[56] References Cited

U.S. PATENT DOCUMENTS

| | | | |
|---|---|---|---|
| 1,967,927 | 7/1934 | Deutsch | 604/20 |
| 3,163,166 | 12/1964 | Brant et al. | 604/20 |
| 3,677,268 | 7/1972 | Reeves | 604/20 |
| 3,749,784 | 7/1973 | Johnson | 514/863 |
| 4,141,359 | 2/1979 | Jacobsen et al. | 604/20 |

FOREIGN PATENT DOCUMENTS

| | | |
|---|---|---|
| 1548621 | 7/1979 | United Kingdom . |
| 2012260 | 7/1979 | United Kingdom . |
| 1596235 | 8/1981 | United Kingdom . |
| 1603384 | 11/1981 | United Kingdom . |
| 2116037 | 9/1983 | United Kingdom . |

OTHER PUBLICATIONS

Acta. Neuro. Scandinav. 66, pp. 401–412, 1982.

Primary Examiner—Ronald W. Grifffin
Attorney, Agent, or Firm—Karl F. Ross; Herbert Dubno

[57] ABSTRACT

A method of treating chronic pain is disclosed which comprises the step of topically administering to the skin of a human patient, 1 to 100 μg/cm$^2$ of body surface of a compound of the Formula (I)

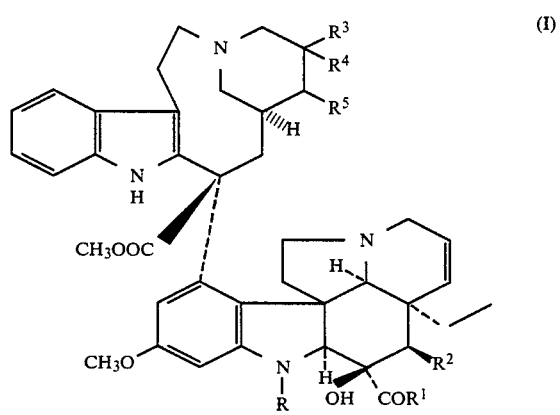

in which
R is —CH$_3$ or —CHO
R$^1$ is methoxy or amino;
R$^2$ is hydrogen, hydroxyl or acetoxy;
R$^3$ is hydrogen or ethyl;
R$^4$ and R$^5$ together form a valency bond or an epoxy bridge, or R$^4$ is hydroxy or ethyl; and
R$^5$ is hydrogen; or a pharmaceutically acceptable acid addition salt thereof, by iontophoresis.

4 Claims, 1 Drawing Figure

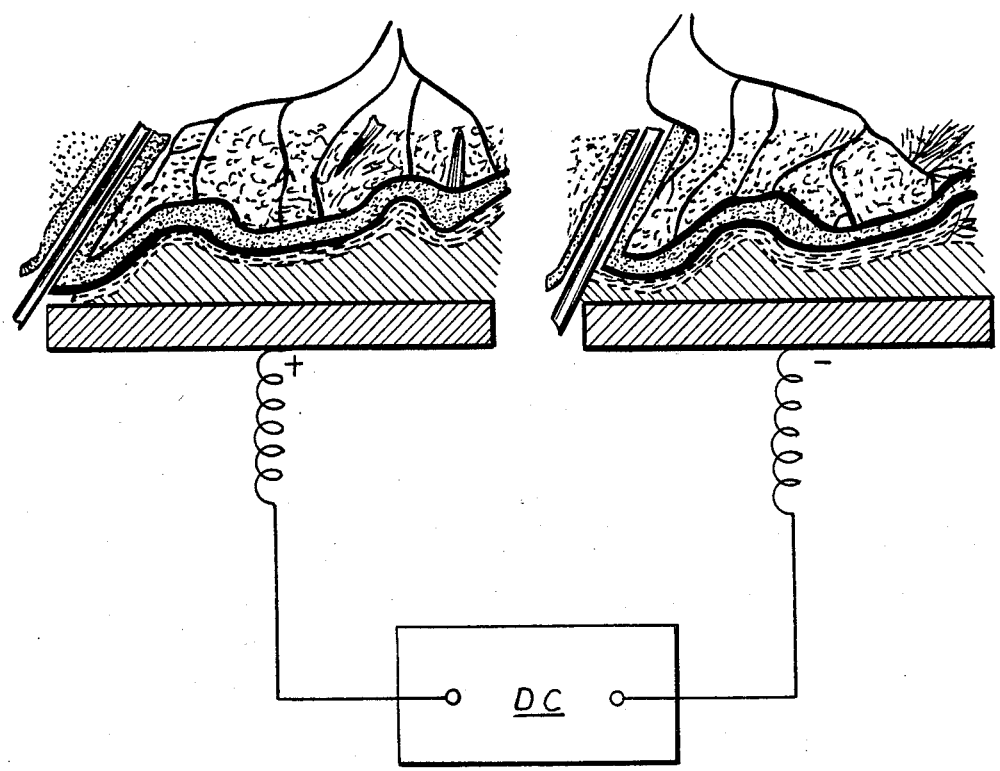

IONTOPHORESIS INTERMEDIARY MATERIAL AND CONTACT SOLUTION FOR THE TREATMENT OF CHRONIC PAIN SYNDROMES

The invention relates to an iontophoresis intermediary material for the treatment of chronic pain syndrome, which comprises as an active ingredient a pharmaceutically acceptable acid addition salt or a protonated derivative of a microtubule inhibitor. More particularly, the invention concerns an iontophoresis intermediary material comprising one or more absorbent layers, which contains a pharmaceutically acceptable acid addition salt or a protoned derivative of at least one microtubule inhibitor of the formula (I)

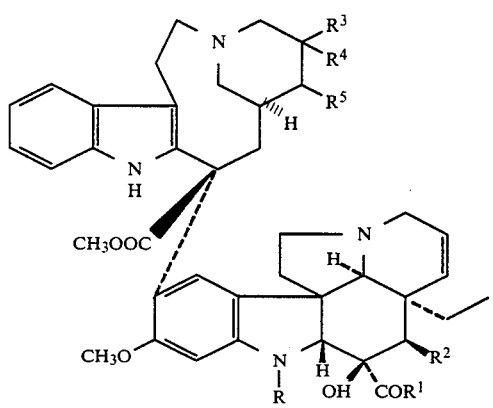

in which
R is —CH$_3$ or —CHO
R$^1$ is methoxy or amino;
R$^2$ is hydrogen, hydroxyl or acetoxy;
R$^3$ is hydrogen or ethyl;
R$^4$ and R$^5$ together form a valency bond or an epoxy bridge; or
R$^4$ is hydroxyl or ethyl; and
R$^5$ is hydrogen,
in the layer to be contacted with the skin surface. The amount of the active substance is about 0.01 to 300 µg/cm$^2$.

According to another aspect of the invention there is provided a contact solution for providing an electric contact between an iontophoresis electrode and the skin surface, which comprises a permeability increasing compound and a pharmaceutically acceptable acid addition salt or a protonated derivative of at least one microtubule inhibitor of the formula (I).

According to still another aspect of the invention there is provided a method of treating pain syndrome, which comprises administering to the patients to be treated at least one microtubule inhibitor of the formula (I) by iontophoresis or perineurally.

Preferred representatives of the compounds of formula (I) include vinblastine, dexacetoxyvinblastine, vincristine, vindesine, leurosine and N-formyl-leurosine. These compounds are preferably employed in the form of their pharmaceutically acceptable, water-soluble salts.

Compounds of the formula (I) are known in the art and their cytostatic properties have also been described. In particular vincristine, vinblastine, vindesine and N-formyl-leurosine have been reported to be therapeutically useful.

Vincristine and vinblastine have been employed also for the treatment of psoriases (U.S. Pat. No. 3,749,784). According to this patent an ointment or a glycerinic solution containing 0.05% of vincristine or vinblastine is applied to the skin surface to be treated.

We have surprisingly found that chronic or otherwise intractable pain syndrom, e.g. trigeminal, postherpetic, paresthetic and ischaemic neuralgia, alcoholic and diabetic polyneuropathy, meralgia, brachialgia, discopathia, arthropathia and terminal pain, etc. can be succesfully treated with the compounds of the formula (I) when applied iontophoretically or perineurally. Transcutaneous iontophoresis of microtubule inhibitors of the formula (I) induces transganglionic degenerative atrophy of the central terminals of primary nociceptive neurons via blockade of axoplasmic transport in the peripheral sensory nerves.

As a consequence, an exceptional pain-killing effect is produced.

It has further been found that the iontophoretically applied microtubule inhibitors do not leak into the blood circulation and accordingly do not affect the blood cell count, the ionogram and the ECG-curve.

The iontophoretically applied microtubule inhibitors do not harm the skin at the site of application and in this manner can successfully replace the more drastic therapeutic methods.

As stated above, the invention relates to an iontophoresis intermediary material for the treatment of chronic pain syndrome which contains as an active ingredient a pharmaceutically acceptable acid addition salt or a protonated derivative of a microtubule inhibitor of the formula (I) in an amount of 0.01 to 300 µg/cm$^2$.

According to the invention the active ingredient is applied to the skin surface to be treated by iontophoresis, via an iontophoresis intermediary material as defined hereinabove. The intermediary material contains 0.01 to 300, preferably 1 to 100 µg/cm$^2$ of active ingredient.

The size and shape of the intermediary material preferably corresponds to the size and shape of the part of the body or body surface to be treated. The intermediary material contains one or more absorbent layers, preferably made of textile, sponge, gauze, lint, paper, artificial cotton, etc. Any material suitable for making a contact between the iontophoresis electrode and the skin surface to be treated can be employed, the intermediary material contains a solution of the active ingredient.

The intermediary material can be prepared well or just before the treatment and if desired, its treatment with the active ingredient can be repeated during the iontophoretic application either by wetting or by impregnating the dry intermediary material having a suitable size and shape with a solution of the active ingredient to be applied. Wetting can be performed by spraying or any other suitable way. If the intermediary material is prepared in a ready for use form, well before its application, in case of an appropriate packing and storing, it can be stored for a long time without any change.

Alternatively, the intermediary material may contain the active ingredient in a dry form, and it can be soaked in the suitable solvents immediately before application. The solvents can be marketed in the same package as the intermediate substance, or separately.

Preferably aqueous solutions of the active ingredients are employed, in which the concentration of the active ingredient and the exact composition depend on the way of the preparation of the intermediary material.

According to a preferred embodiment, a solution of the active ingredient is sprayed onto a contact layer wetted with tepid water. In this case the solution preferably contains 0.001 to 0.5% of active ingredient, and optionally 1 to 10% of a permeability increasing substance. If the article is prepared in a different way, the composition of the solution employed may also be different, depending on the quality of the intermediary material. The solution used for impregnation is prepared in a known manner.

BRIEF DESCRIPTION OF THE DRAWING

The sole FIGURE in the case is a diagram of an iontophoresis apparatus. The patient's skin is in contact with an intermediary material which in turn is in contact with each of the positive and negative poles of the electrodes.

Iontophoresis is performed with the aid of lead electrodes. The size and shape of the positive electrode corresponds to the size and shape of the areas to be treated, and its thickness preferably is 0.5 to 2 mm. An intermediary material of a suitable size and shape is wetted with tepid water and treated with the active ingredient to be used, whereupon it is placed on the dermatome to be treated. The electrode is placed on the top of the intermediary layer, taking care that the electrode should not have a direct contact with the skin. The surface of the intermediary material depends on the size of the dermatome to be treated but preferably is between 10 and 2000 cm$^2$. The negative electrode is placed on an optional place of the dermatome, placing a wet textile between the skin and the electrode. The iontophoresis is preferably performed with a Nervostat ® apparatus, providing a direct current. If the neck or the head is to be treated, iontophoresis is carried out at 1 to 10 mA d.c., the current intensity is slowly increased to peak value and is stopped when the patient has an unpleasant feeling. The limbs and the trunk are treated at 10 to 30 mA d.c., otherwise under the above conditions. Iontophoresis takes 10 to 80, preferably 30 to 60 minutes. If small electrodes are employed (as in the case of trigeminal neuralgy) the fabric is generally sprayed with the solution of the active ingredient every quarter hour to avoid drying out. Treatment is performed repeatedly, in certain intervals. Preferably after a daily treatment for five days the treatment is ceased for 1 to 3, preferably 2 days. A total cure lasts for 10 to 60 days, preferably 26 days (20 treatments and 6 days when the treatment is ceased). In certain cases, for example in the case of trigeminal neuralgia, longer cures may also be necessary.

Our results in connection with the transganglionic degenerative atrophy (trggl. deg. atr.) of the central terminals of primary nociceptive neurons, via blockade of the axoplasmic transport in the peripheral sensory nerves open entirely new paths for pain therapy. The iontophoretically applied microtubule inhibitors are practically devoid of any toxicity. Both the radiochemical experiments and the constant blood cell counts and ionogram of patients treated iontophoretically support this statement. Neither in the blood nor in the urine could we trace any radioactivity within 3 hours following a one-hour treatment with N-formyl-leurosine sulfate labelled with $^{14}$C in the formyl group.

The blood cell count, the electrocardiogram and the ionogram were controlled weekly for every patient during the electrophoresis therapy. The values were controlled again 3 and 6 months after treatment. We have found no significant change in any of these parameters. Moreover, we have observed no pathological alteration of the skin after iontophoresis.

Both the animal tests and the human experiments produced significantly better results than any of the hitherto known therapies. The animal and human tests are in full conformity.

Clinical tests showed that even the pain syndrom due to the most stubborn neuralgiae disappeared by the end of the third week of treatment. Some of the patients voluntarily interrupted the treatment after about one week, since the pain they had suffered from were substantially reduced after a 6-day treatment. In such cases the pain recurred after about 3 to 4 weeks and a second series of treatments had substantially less dramatic effect than the first treatment carried out continuously, without any intermission.

EXPERIMENTS

I. Hot-plate test

It is well known that perineural application results in degenerative atrophy. Therefore, the extent of the resulting pain-reduction was examined.

13 female rats, 200-250 g. in body weight, were subjected to the hot-plate test. Micrutubule inhibitors were applied by means of the cuff technique around both sciatic nerves for 30 minutes. Cuffs were prepared from the artificial fibrin sponge Gelaspon ® (Jenapharm, GDR), and the sciatic nerve was set free under Nembutal anaesthesia.

In the case of 6 animals intermediary materials (cuffs) soaked with a 1% physiological saline solution of 50 μg of vinblastine sulfate were applied around both sciatic nerves.

In case of the remaining 7 rats both sciatic nerves were surrounded by a similar cuff soaked in a physiological saline solution.

Thirty minutes later the cuff was removed and the wound was closed with a silk suture. The time latency until licking the hind paw was recorded in seconds and the results were evaluated by means of Student's t-test. The time latency was recorded daily, the results of the single experiments were cummulated and evaluated statistically. The statistical analysis of the reaction times of the rats treated with vinblastine sulfate showed a significant difference from the latency of the rats treated with a physiological saline solution. Starting with the 10th day of the experiment the time between the stimulus and the reaction has gradually been increased to 2-3 times that of the values observed in case of the control rats (Table I).

TABLE I

The effect of transganglionary degenerative atrophy on the latency of the paw-licking reflex of female rats
Hot-plate test (54° C.)

| Group | No. | Cuff treatment | Average sec. | Standard deviation sec | Standard error sec |
|---|---|---|---|---|---|
| A | 1 | physiological saline | 13.7 | 5.1 | 1.9 |
|   | 2 | physiological saline | 11.3 | 3.1 | 1.7 |
|   | 3 | physiological saline | 9.4 | 1.6 | 0.6 |
|   | 4 | physiological saline | 10.6 | 3.1 | 1.2 |
|   | 5 | physiological saline | 13.1 | 4.5 | 1.7 |
|   | 6 | physiological saline | 10.7 | 3.4 | 1.3 |
|   | 7 | physiological saline | 12.0 | 4.2 | 1.6 |
| B | 8 | Vinblastine sulfate | 43.0 | 13.8 | 2.7 |
|   | 9 | Vinblastine sulfate | 29.4 | 15.8 | 2.3 |

TABLE I-continued

The effect of transganglionary degenerative atrophy
on the latency of the paw-licking reflex of female rats
Hot-plate test (54° C.)

| Group No. | Cuff treatment | Average sec. | Standard deviation sec | Standard error sec |
|---|---|---|---|---|
| 10 | Vinblastine sulfate | 31.7 | 13.2 | 1.6 |
| 11 | Vinblastine sulfate | 31.2 | 18.1 | 2.7 |
| 12 | Vinblastine sulfate | 31.3 | 17.0 | 3.0 |
| 13 | Vinblastine sulfate | 37.0 | 15.3 | 2.7 |

The result of the t-test between the groups A (1–7) and B (8–13): significant difference at a 99% level;
$p < 0.001$
degree of freedom: 11;
t-value: $-11.0329$ Two rats were observed 80 days after the termination of the treatment with a cuff soaked with vinblastine sulfate. After the 70th postoperative days the latency time was gradually decreased and approached that of the control animals (Table II).

TABLE II

The effect of synaptic restitution on the latency of the hind paw licking reflex of female rats

| No. of animals | active ingredient | 10–70th day after operation | | | 70–80th day after operation | | |
|---|---|---|---|---|---|---|---|
| | | average (sec) | standard deviation (sec) | standard error (sec) | average (sec) | standard deviation (sec) | standard error (sec) |
| 12 | vinblastine sulfate | 31.3 | 17.0 | 3.0 | 12.9 | 2.6 | 0.6 |
| 13 | vinblastine sulfate | 37.0 | 15.3 | 2.7 | 17.2 | 2.2 | 0.7 |

II. Radiochemical assay of the skin after iontophoretic application of $^{14}$C-labelled microtubule inhibitor In order to show that microtubule inhibitors are, in fact, transported transcutaneously, wet gauze was sprayed with ($^{14}$C)-formyl leurosine sulfate with a specific activity of 15 μCi. Rats were anaesthized with Nembutal (sodium 5-ethyl-5-(1-methylbutyl)-barbiturate) and electrophoresis was performed with a 14 mm diameter round lead electrode, and direct current (max. 5 mA) obtained from a Nervostat ® equipment, on the abdominal skin. The treated area was about 2 to 12 cm². The positive pole of the Nervostat ® apparatus was connected with the electrophoresis electrode having an area of 6 cm² and was covered with a gauze soaked in a solution containing the active ingredient in 5 ml. of a 5% dimethyl sulfoxide solution. The negative pole was attached to the indifferent electrode (12 cm²), which was surrounded by gauze soaked in a physiological saline solution and applied to the depilated hairy skin contralaterally. The current was slowly increased to peak value. During electrophoresis, the animals were kept under close surveillance and, if necessary, the positions of the electrodes were corrected. Iontophoresis was performed for one hour. The animals were then decapitated and the skin under the electrode was excised. Cryostat section of a thickness of 25μ were obtained parallel to the surface, solubilized with Soluene and the cpm-e determined with a Packard liquid scintillation apparatus. The results obtained are shown in Table III.

The results listed in Table III prove while less than 1% of the ($^{14}$C)-formyl-leurosine applied to the electrode infiltrated various layers of the skin, only about one-fifth of this (0.2% of the total amount) reached the layer of the skin supplied with sensory nerve endings.

TABLE III

Distribution of radioactivity in rat skin 1 h after iontophoretic application of $^{14}$C—formylleurosine

| | |
|---|---|
| Total amount applied at the electrode: | 4,890,000 cpm |
| Total amount revealed in the skin: | 36,500 cpm |
| % distribution of radioactivity in the skin: | |
| Stratum corneum | 54% |
| Stratum planocellulare } Stratum lucidum } Stratum granulosum } | 24% |
| Stratum germinativum } Papillae, superficial layer } | 11% |
| Papillae, deep layer } Cutis } | 10% |

III. Clinical trials

Fifty-one patients suffering from various chronic pain syndroms, were subjected to daily vinblastine or vincristine sulfate iontophoresis for 8–24 days. The parameters of the treatment are set forth in Table IV below.

TABLE IV

Paradigm of iontophoresis therapy (FIG. 1)

| | |
|---|---|
| Concentration of microtubule inhibitors: | 0.01% vinblastine or 0.001% vincristine |
| Solvent: | Isotonic saline + 5% dimethyl sulfoxide |
| Volume: | 100 ml. |
| Current: | DC, 10–30 mA for dermatomes of trunk and limbs 2–5 mA for dermatomes of the head |
| Electrodes: | Lead, 1 mm thick; size 20 by 40 cm (for dermatomes of trunk and limbs) or 10 by 15 cm for dermatomes of the head |
| Intermediary: | Hydrophilic fabric (textile) |
| Sessions: | 1 h daily for 8–24 days |

Prior to treatment, patients were instructed regarding the essence of Vinca alkaloid iontophoresis and required to sign a statement of their informed consent. The treatment was started with placebo iontophoresis for 7–14 days (with saline). Patients were requested to express improvement, if any, in their pain state in percentages; in this score 100% means total relief of pain, 0% means no change and negative percentages mean worsening. While placebo iontophoresis had no effect in any case, patients reported improvement in their pain state as a rule on the 5th to 7th day of Vinca alkaloid iontophoresis. Based on a follow-up for one year, 40 patients were completely and permanently relieved of pain by vinblastine or vincristine sulfate iontophoresis to the dermatomes where pain was registered or referred to, in 8 other patients, relief of pain was partial or temporary, and in 3 cases, the treatment was entirely ineffective (Table V.)

Taking into account that the patients had previously participated in the usual forms of pain therapy, including opiates, Tegretol and infiltration therapy, iontophoresis with dionine and histamine and even neurosurgery (exhairesis), but without any major results, the results obtained by the iontophoresis according to the invention are highly surprising. An important aspect to iontophoresis with the compounds of the formula (I) is that it affects pathological pain without inducing anesthesia or analgesia of the skin.

TABLE V

CHRONIC PAIN PATIENTS TREATED BY VINCA ALKALOID IONTOPHORESIS.
FOLLOW-UP PERIOD: ONE YEAR

| Diagnosis | No. of patients | Age of patients (years) | Duration of persistent pain before iontophoretic vinblastine treatment | No. of patients relieved of pain | Estimated degree of relief in percentages (subjective estimation by successfully treated patients) | No effect |
|---|---|---|---|---|---|---|
| Postherpetic neuralgia | 11 | 39–82 (average: 66) | 3 wk–4 yr (average: 8 mo) | 11 | 70–100% (average: 96%) | — |
| Causalgia, paresthetic, meralgic and intercostal neuralgia | 7 | 36–80 (average: 50) | 6 wk–19 yr (average: 3 yr) | 7 | 40–100% (average: 91%) | — |
| Metabolic (alcoholic and diabetic) polyneuropathy | 5 | 45–63 (average: 54) | 2 mo–2 yr (average: 1 yr) | 5 | 100% | — |
| Trigeminal neuralgia (Tic douloureux) | 15 | 48–74 (average: 60) | 7 mo–17 yr (average: 6 yr) | 14* | 60–100% (average: 92%) | 1 |
| Terminal pain | 7 | 33–71 (average: 48) | 5 wk–1 yr (average: 14 wk) | 6 | 80–100% (average: 95%) | 1 |
| Discopathy (after surgery) | 4 | 45–67 (average: 57) | 3 mo–4 yr (average: 1.5 yr) | 3 | 100% | 1 |
| Osteoarthritic pain | 2 | 55–73 (average: 64) | 7 mo–5 yr (average: 3 yr) | 2 | 100% | — |

*Relapses in 5 cases; pain alleviated by repeated iontohoretic treatment.

The vinblastine sulfate-containing contact solution, the intermediary material and their application are illustrated by the following Examples, which are not intended to restrict the scope of the invention in any way.

EXAMPLE 1

Gauze, the size and shape of which corresponds to the size and shape of the electrode to be employed is wetted with tepid water, and sprayed with a solution having the following composition, in an amount of 0.5 ml. of solution/cm².

| Composition of the solution: | |
|---|---|
| vinblastine sulfate | 5 mg |
| physiological sodium chloride solution | 30 ml. |
| 10% dimethyl sulfoxide | 20 ml. |

The article obtained is applied to the skin while wet.

EXAMPLE 2

The procedure described in Example 1 is followed, except that the solution contains 0.5 to 5 mg. of vincristine sulfate in place of vinblastine sulfate.

EXAMPLE 3

The procedure described in Example 1 is followed except that the solution contains 10 mg of N-desmethyl-N-formyl-leurosine sulfate in place of vinblastine sulfate.

EXAMPLE 4

The procedure described in Example 1 is followed except that the solution contains 15 mg. of vindesine sulfate instead of vinblastine sulfate.

EXAMPLE 5

The procedure described in Example 1 is followed, except that the solution contains 10 mg. of desacetoxy vinblastine sulfate instead of vinblastine sulfate.

We claim:

1. A method of treating a chronic pain syndrome in a human, which comprises the step of topically administering to the skin of the human 1 to 100 μg/cm² of body surface of a compound of the Formula (I)

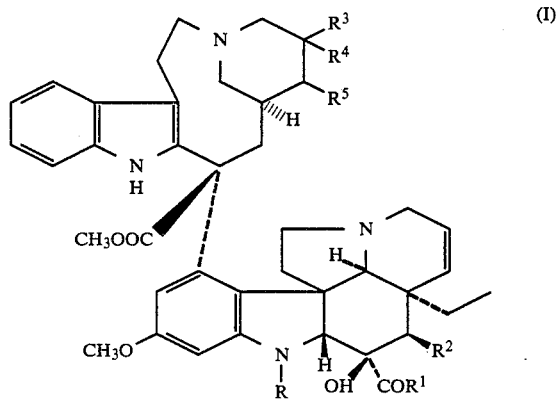

in which
R is —CH₃ or —CHO;
R¹ is methoxy or amino;
R² is hydrogen, hydroxyl or acetoxy;
R³ is hydrogen or ethyl;
R⁴ and R⁵ together form a valency bond or an epoxy bridge, or R⁴ is hydroxyl or ethyl; and
R⁵ is hydrogen;

or a pharmaceutically acceptable acid addition salt thereof, by iontophoresis.

2. The method of treating a chronic pain syndrome defined in claim 1 wherein the compound of the Formula (I) is vinblastine in the form of its sulfate acid addition salt.

3. The method of treating a chronic pain syndrome defined in claim 1 wherein the compound of the Formula (I) is vincristine in the form of its sulfate acid addition salt.

4. The method of treating a chronic pain syndrome defined in claim 1 wherein the chronic pain syndrome is postherpetic neuralgia.

* * * * *